US008523828B2

(12) United States Patent
Callahan

(10) Patent No.: US 8,523,828 B2
(45) Date of Patent: Sep. 3, 2013

(54) CLAMPING ASSEMBLY FOR USE WITH A CATHETER

(75) Inventor: Mark Callahan, Medway, MA (US)

(73) Assignee: Covidien LP, Mansfield, MA (US)

( * ) Notice: Subject to any disclaimer, the term of this patent is extended or adjusted under 35 U.S.C. 154(b) by 471 days.

(21) Appl. No.: 12/636,285

(22) Filed: Dec. 11, 2009

(65) Prior Publication Data

US 2010/0168680 A1   Jul. 1, 2010

Related U.S. Application Data

(60) Provisional application No. 61/141,529, filed on Dec. 30, 2008.

(51) Int. Cl.
*A61M 5/00* (2006.01)
(52) U.S. Cl.
USPC .................. 604/250; 251/9; 251/10; 604/34
(58) Field of Classification Search
USPC ................................ 604/250, 34; 251/9–10
See application file for complete search history.

(56) References Cited

U.S. PATENT DOCUMENTS

| 1,330,523 | A |   | 2/1920 | Evitts et al. |
|---|---|---|---|---|
| 1,959,074 | A |   | 5/1934 | Bloxsom |
| 2,285,821 | A | * | 6/1942 | Maloney ............................ 251/4 |
| 2,595,511 | A |   | 5/1952 | Butler |
| 2,844,251 | A |   | 7/1958 | Smith |
| 3,429,549 | A |   | 2/1969 | Swanson |
| 4,248,401 | A |   | 2/1981 | Mittleman |
| 4,292,969 | A |   | 10/1981 | Raible et al. |
| 4,306,705 | A |   | 12/1981 | Svensson |
| 4,307,869 | A |   | 12/1981 | Mittleman |
| 4,434,963 | A |   | 3/1984 | Russell |
| 4,439,179 | A |   | 3/1984 | Lueders et al. |
| 4,560,378 | A |   | 12/1985 | Weiland |
| 4,570,898 | A |   | 2/1986 | Staeubli |
| 4,586,691 | A |   | 5/1986 | Kozlow |
| 4,660,802 | A | * | 4/1987 | Oscarsson ........................ 251/9 |
| 4,932,629 | A |   | 6/1990 | Rodomista et al. |

(Continued)

FOREIGN PATENT DOCUMENTS

DE   3324699   12/1984
DE   9408633 U1   10/1994

(Continued)

OTHER PUBLICATIONS

International Search Report dated Jun. 16, 2010 in copending PCT Appln. No. PCT/US2010/030978.

(Continued)

*Primary Examiner* — Kevin C Sirmons
*Assistant Examiner* — Edelmira Bosques
(74) *Attorney, Agent, or Firm* — John Paul Mello, Esq.

(57) ABSTRACT

A clamping assembly includes a body having a base and an arcuate body portion secured to the base. The arcuate body portion defining at least one opening dimensioned to receive a tubular member having a lumen. The clamping assembly further includes a slide member adapted to slide along the arcuate portion between an open position and a closed position. The slide member is movable along the arcuate body portion to compress the tubular member received within the body against the base to obstruct the lumen of the tubular member when the slide member is in the closed position.

12 Claims, 5 Drawing Sheets

(56) References Cited

U.S. PATENT DOCUMENTS

| | | |
|---|---|---|
| 4,950,255 A | 8/1990 | Brown et al. |
| 5,035,399 A | 7/1991 | Rantanen-Lee |
| 5,071,411 A | 12/1991 | Hillstead |
| 5,158,553 A | 10/1992 | Berry et al. |
| 5,257,770 A | 11/1993 | Grove |
| 5,257,978 A | 11/1993 | Haber et al. |
| 5,318,546 A | 6/1994 | Bierman |
| 5,352,214 A | 10/1994 | Oscarsson |
| 5,423,769 A | 6/1995 | Jonkman et al. |
| 5,489,274 A | 2/1996 | Chu et al. |
| 5,853,398 A | 12/1998 | Lal et al. |
| 6,217,564 B1 | 4/2001 | Peters |
| 6,536,739 B1 | 3/2003 | Jensen |
| 6,592,558 B2 | 7/2003 | Quah |
| 6,610,027 B1 | 8/2003 | El Hatu |
| 6,689,109 B2 | 2/2004 | Lynn |
| 6,742,760 B2 | 6/2004 | Blickhan et al. |
| 7,011,645 B2 | 3/2006 | McGuckin, Jr. et al. |
| 7,018,374 B2 | 3/2006 | Schon et al. |
| 7,094,218 B2 | 8/2006 | Rome et al. |
| 7,182,746 B2 | 2/2007 | Haarala et al. |
| 7,306,586 B2 | 12/2007 | Beaufore et al. |
| 7,311,697 B2 | 12/2007 | Osborne |
| 7,364,571 B2 | 4/2008 | Schinazi et al. |
| 7,381,204 B2 | 6/2008 | Wilson et al. |
| 2002/0062106 A1 | 5/2002 | Chu et al. |
| 2003/0040724 A1 | 2/2003 | Lynn |
| 2003/0225379 A1 | 12/2003 | Schaffer et al. |
| 2004/0064086 A1 | 4/2004 | Gottlieb et al. |
| 2004/0171997 A1 | 9/2004 | Wilson et al. |
| 2004/0186445 A1 | 9/2004 | Raulerson et al. |
| 2004/0249349 A1 | 12/2004 | Wentling |
| 2005/0256447 A1 | 11/2005 | Richardson et al. |
| 2006/0015074 A1 | 1/2006 | Lynn |
| 2006/0081797 A1 | 4/2006 | Zerfas |
| 2006/0149214 A1 | 7/2006 | Breiter et al. |
| 2006/0189922 A1 | 8/2006 | Amarasinghe et al. |
| 2007/0112313 A1 | 5/2007 | Fangrow |
| 2007/0225682 A1 | 9/2007 | Ash et al. |
| 2007/0255229 A1 | 11/2007 | Kane et al. |
| 2008/0021415 A1 | 1/2008 | Durkin et al. |
| 2008/0029721 A1 | 2/2008 | Miyahara |
| 2008/0051731 A1 | 2/2008 | Schweikert et al. |
| 2008/0082080 A1 | 4/2008 | Braga |
| 2009/0005759 A1 | 1/2009 | Chelak |
| 2009/0030378 A1 | 1/2009 | Garcia, Jr. |

FOREIGN PATENT DOCUMENTS

| | | |
|---|---|---|
| EP | 1360973 A1 | 11/2003 |
| JP | 2006-255397 | 9/2006 |
| WO | WO 97/11296 | 3/1997 |

OTHER PUBLICATIONS

European Search Report mailed Apr. 9, 2010 by the European Patent Office in copending European Patent Application No. 09180737.0.

* cited by examiner

CLAMPING ASSEMBLY FOR USE WITH A CATHETER

This application claims priority from U.S. provisional application Ser. No. 61/141,529 filed Dec. 30, 2008, the entirety of which is incorporated herein by reference.

BACKGROUND

1. Technical Field

The present disclosure generally relates to a clamp for obstructing flow through a fluid conduit, and, in particular, relates to clamping assemblies for obstructing fluid flow through extension tubes of a catheter assembly.

2. Description of the Related Art

Catheters are flexible medical devices that facilitate the withdrawal and introduction of fluids from and to body cavities, ducts, and vessels. Catheters may have particular application in a hemodialysis procedure where blood is withdrawn from a blood vessel for treatment, and subsequently returned to the blood vessel for circulation. Known hemodialysis catheters include multiple lumens, such as dual lumen or triple-lumen catheters, which permit bi-directional fluid flow within the catheter whereby one lumen is dedicated for withdrawal of blood from a vessel and the other lumen is dedicated for returning treated blood to the vessel. During an exemplary hemodialysis procedure, a multiple lumen catheter is inserted into a body vessel and blood is withdrawn through an arterial lumen of the catheter. The removed blood is directed to a hemodialysis unit which dialyzes, or purifies, the blood to remove waste and toxins from the blood. The dialyzed blood is returned to the patient through a venous lumen of the catheter.

Catheter assemblies often have one or more extension tubes. In hemodialysis and other medical procedures, clinicians clamp the extension tubes to occlude flow at certain stages of a medical procedure. In addition, clamping of the extension tubes is usually required in between medical procedures. A low-profile clamp that rests comfortably against the patient's skin would provide an improved quality of life. A number of clamps have been developed over the years. Improvements to known clamps that can provide a more comfortable patient experience are desirable.

SUMMARY

The present disclosure relates to a clamping assembly. This clamping assembly includes a body having a base and an arcuate body portion secured to the base. The arcuate body portion defining at least one opening dimensioned to receive a tubular member having a lumen. The clamping assembly further includes a slide member adapted to slide along the arcuate portion between an open position and a closed position. The slide member is movable along the arcuate body portion to compress the tubular member received within the body against the base to obstruct the lumen of the tubular member when the slide member is in the closed position.

In one embodiment, the base is flat and adapted to support the tubular member.

In one embodiment, the arcuate body portion is secured to the ends of the base.

In one embodiment, a lateral open space is defined between the flat base and the arcuate body portion.

In one embodiment, at least one opening includes a first opening and an aperture dimensioned to receive the tubular member, the aperture being located in a first section of the arcuate body portion.

In one embodiment, the clamping assembly further includes a second opening located in a proximal section of the arcuate body portion.

In one embodiment, the arcuate body portion includes at least one feature which is releasably engagable with a corresponding feature on the slide member to releasably secure the slide member in the closed position.

In one embodiment, the arcuate body portion includes a plurality of detents, each detent being adapted to secure the slide member at a predetermined secured position along the arcuate body portion.

In one embodiment, the slide member includes an engagement member configured to releasably engage a detent of the plurality of detents to retain the slide member in relation to the arcuate body portion.

In one embodiment, the slide member includes a first portion facing away from the base and a second portion facing toward the base, the first portion including the engagement member.

In one embodiment, the second portion of the slide member includes a blunt protuberance configured to compress the tubular member.

In one embodiment, the first and second portions of the slide member are configured to spread apart when the slide member moves between the predetermined secured positions.

In one embodiment, the clamping assembly further includes a track positioned along the arcuate body portion, wherein the track is configured to slidably receive the second portion of the slide member to facilitate movement of the slide member along the arcuate body portion.

In one embodiment, the slide member is made of a resilient material.

In one embodiment, the slide member has a substantially C-shape.

In one embodiment, the plurality of detents includes a detent positioned to retain the slide member at an intermediate position between the open and closed positions.

The present disclosure further relates to a catheter assembly including a catheter defining a bore, a body, and a slide member. The body has a base and an arcuate body portion secured to the base. The base is configured to support the catheter. The slide member is slidably positioned on the arcuate body portion. The slide member is adapted to slide along the arcuate body portion between an open position and a closed position. The slide member is movable along the arcuate body portion to compress the catheter to occlude the bore when the slide member is in the closed position.

In one embodiment, the body defines at least one opening dimensioned to receive the catheter.

In one embodiment, the arcuate body portion includes a plurality of detents, each detent being adapted to secure the slide member at a predetermined secured position.

In one embodiment, the slide member includes an engagement protrusion configured to securely engage a detent of the plurality of detents to fix the position of the slide member along the arcuate portion at the predetermined secured positions.

In one embodiment, the slide member has a substantially C-shape.

The present disclosure further relates to a clamping assembly including a body and a slide member. The body has a base and an arcuate body portion secured to the base. The arcuate body portion defines a first opening, a second opening located in a proximal section of the arcuate body portion, and an aperture dimensioned to receive a tubular member having a lumen. The aperture is located in a first section of the arcuate body portion. The arcuate body portion includes at least one feature which is releasably engagable with a corresponding feature on the slide member to releasably secure the slide member in the closed position. The slide member is adapted to slide along the arcuate portion between an open position and a closed position. The slide member is movable along the arcuate body portion to compress the tubular member received within the body against the base to obstruct the lumen of the tubular member when the slide member is in the closed position.

BRIEF DESCRIPTION OF THE DRAWINGS

Various embodiments of the presently disclosed clamping assembly are described herein with reference to the accompanying drawings, wherein.

DETAILED DESCRIPTION OF THE EMBODIMENTS

In the discussion that follows, the term "proximal" or "trailing" will refer to the portion of a structure that is closer to a clinician, while the term "distal" or "leading" will refer to the portion that is farther from the clinician. As used herein, the term "subject" refers to a human patient or other animal. The term "clinician" refers to a physician, nurse or other care provider and may include support personnel.

Figure 1:
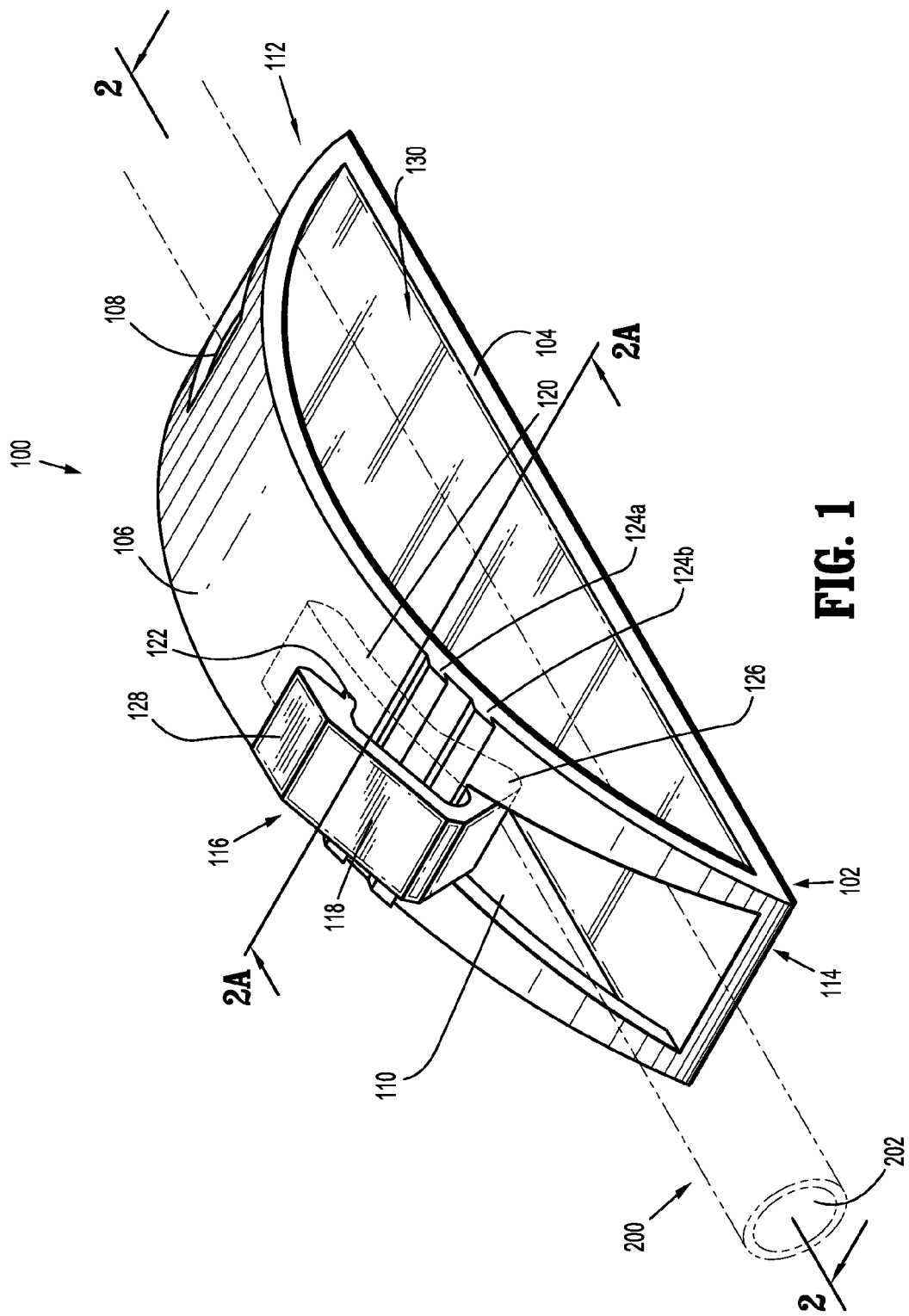
FIG. 1 is a perspective view of a clamping assembly for a catheter in accordance with an embodiment of the present disclosure.

FIG. 1 shows an embodiment of a clamping assembly 100 for clamping a tubular member 200 defining a bore 202, e.g., a catheter, an extension tube, or any other suitable fluid conduit. Clamping assembly 100 includes a body 102 having a flat base 104 and an arcuate body portion 106 secured to flat base 104. Body 102 defines lateral open spaces 130 on each side of body 102 to facilitate visualization of tubular member 200 during operation of clamping assembly 100. Lateral open spaces 130 are defined between arcuate body portion 106 and flat base 104. Flat base 104 is adapted to support at least a portion of tubular member 200 along its inner surface. In use, flat base 104 may rest on a subject's skin while the clinician performs the appropriate medical procedure. Arcuate body portion 106 has a proximal section 112 and a distal section 114. Only proximal and distal sections 112, 114 of arcuate body portion 106 directly contact flat base 104. Arcuate portion 106 further includes an opening 108 located in proximal section 112 and an aperture 110 located in distal section 114. Opening 108 and aperture 110 are both dimensioned to receive tubular member 200. As seen in FIG. 1, opening 108 and aperture 110 together allow passage of catheter 200 through body 102 of clamping assembly 100. Openings 108, 110 can be defined by non-parallel walls as shown in FIG. 1 or alternatively by parallel walls.

Figure 8:
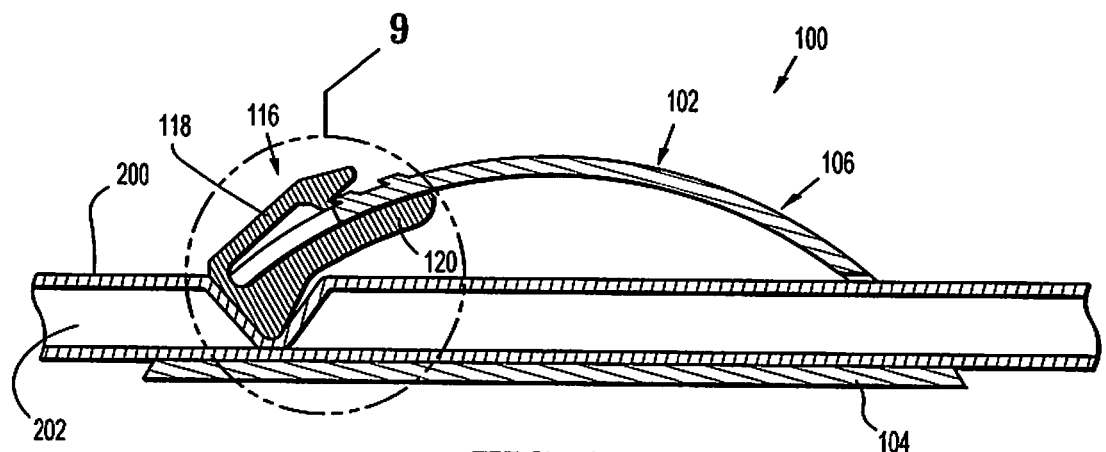
FIG. 8 is a side cross-sectional view of the clamping assembly shown in FIG. 1 with the slide member in the closed position.

Clamping assembly 100 further includes a slide member 116 adapted slide along arcuate portion 106 between an open position (see FIG. 2) and a closed position (see FIG. 8). In the open position, the slide member 116 is spaced above flat base 104 such that slide member 116 does not compress tubular member 200 positioned within body 102 to permit flow through bore 202 of tubular member 200. In the closed position, slide member 116 compresses tubular member 200 and prevents flow through bore 202 of tubular member 200. Slide member 116 features a substantially C-shape and includes a first or upper portion 118 facing away from flat base 104 and a second or lower portion 120 facing flat base 104. In one embodiment, at least a section of lower portion 120 may ride along a track 132 (see FIG. 2A) defined on arcuate body portion 106 to facilitate movement of slide member 116 along arcuate body portion 106.

Slide member 116 and arcuate body portion 106 include corresponding features for frictional or other mechanical engagement to releasably secure slide member 116 in at least a closed position. Examples of engagement features include detents, textured surfaces, and biased locking members. As shown in FIG. 1, first portion 118 of slide member 116 includes downwardly extending engagement protrusion 122 configured to securely engage a stop member or detent 124a or 124b formed on arcuate body portion 106. First portion 118 of slide member 116 includes an engagement member 128 disposed proximal to engagement protrusion 122. Second portion 120 of slide member 116 has a blunt protuberance 126 adapted to compress tubular member 200. In one embodiment, slide member 116 is made of a resilient material and first and second portions 118, 120 are configured to spread apart or expand outwardly when slide member 116 moves between detents 124a, 124b of arcuate body portion 106.

Arcuate body portion 106 includes one or more stop members or detents 124a, 124b disposed at predetermined secured positions. Each detent 124a, 124b is adapted to securely engage engagement protrusion 122 of slide member 116 to fix the position of slide member 116 relative to arcuate portion 106. Detents 124a, 124b allow the clinician to lock slide member 116 at multiple predetermined secured positions along arcuate portion 106. In one embodiment, in the open position, slide member 116 does not engage detents 124a, 124b and therefore is not secured relative to the arcuate portion 106. Alternatively, slide member 116 can engage a detent (not shown) while located in the open position.

Figure 2:
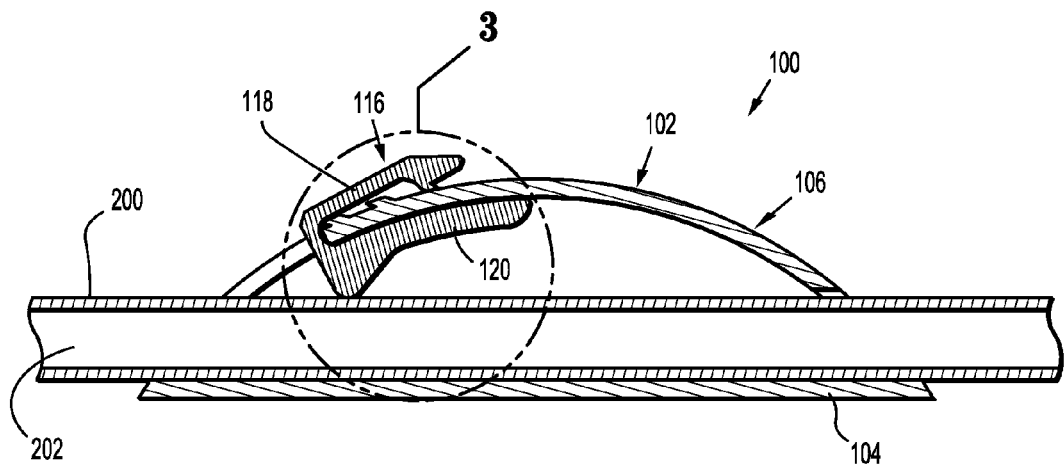
FIG. 2 is a side cross-sectional view of the clamping assembly shown in FIG. 1 with a slide member in an open position.
Figure 2A:
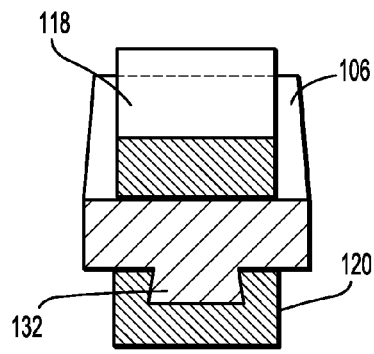
FIG. 2A is a front cross-sectional view of the clamping assembly shown in FIG. 1.
Figure 3:
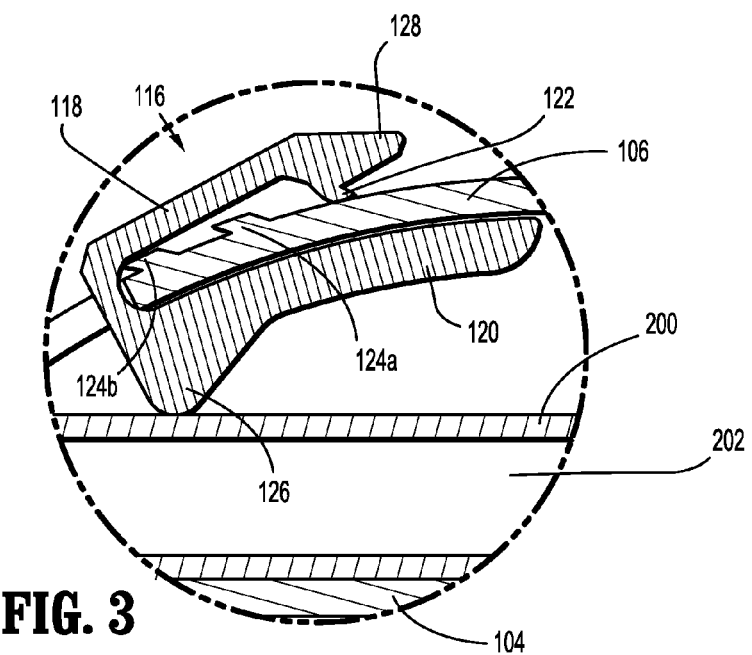
FIG. 3 is an enlarged side cross-sectional view showing the indicated area of detail shown in FIG. 2.

FIGS. 2 and 3 illustrate clamping assembly 100 with slide member 116 located in the open position and tubular member 200 supported by flat base 104. When slide member 116 is disposed in the open position, engagement protrusion 122 does not engage detents 124a, 124b and thus slide member 116 is free to slide along arcuate portion 106. Although blunt protuberance 126 may contact tubular member 200 while slide member is in the open position, blunt protuberance 126 does not press tubular member 200 against flat base 104. As a consequence, slide member 116 does not obstruct flow through bore 202 of tubular member 200.

Figure 4:
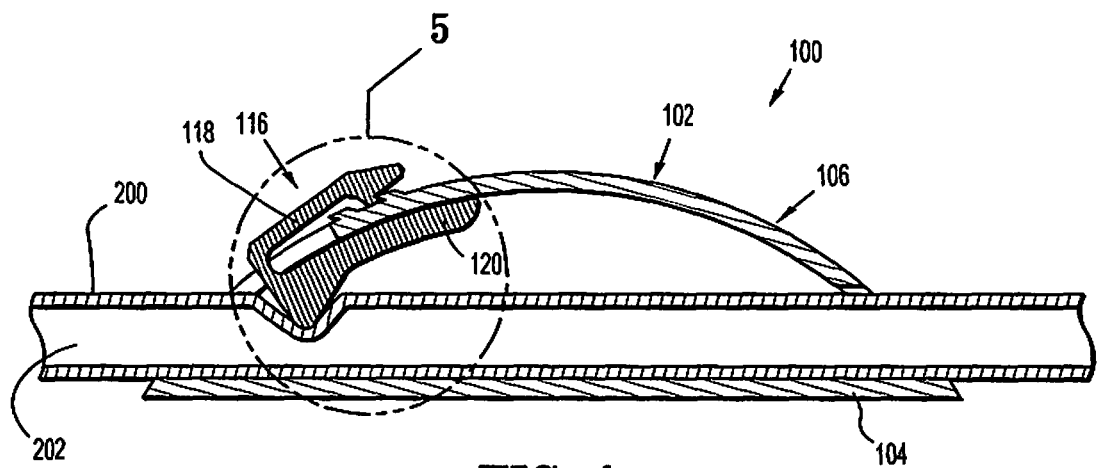
FIG. 4 is a side cross-sectional view of the clamping assembly shown in FIG. 1 with the slide member in an intermediate position.
Figure 5:
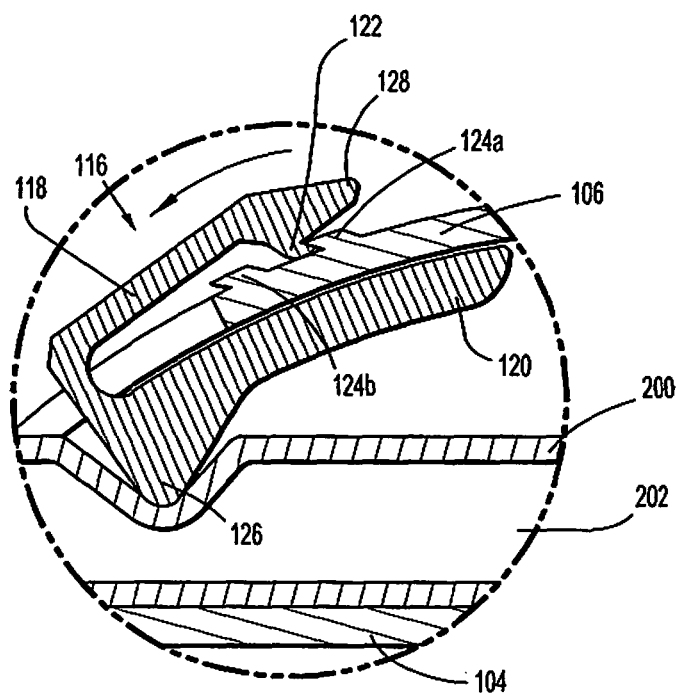
FIG. 5 is an enlarged side cross-sectional view showing the indicated area of detail shown in FIG. 4.

With reference to FIGS. 4 and 5, a clinician can move slide member 116 distally along arcuate body portion 106 from the open position to an intermediate position to progressively close bore 202 of tubular member 200. As slide member 116 moves from the open position to the intermediate position, first and second portions 118, 120 briefly separate from each other while engagement protrusion 122 passes over detent 124a to a position between detents 124a and 124b, i.e, the intermediate position. After engagement protrusion 122 reaches the intermediate position, first and second portions 118, 120 of slide member 116 return to their original position and engagement protrusion 122 securely engages detent 124a to lock slide member 116 in the intermediate position. In the intermediate position, blunt protuberance 126 presses tubular member 200 against flat base 104, partially compressing tubular member 200. As a result, slide member 116 partially occludes flow through bore 202 of tubular member 200.

Figure 6:
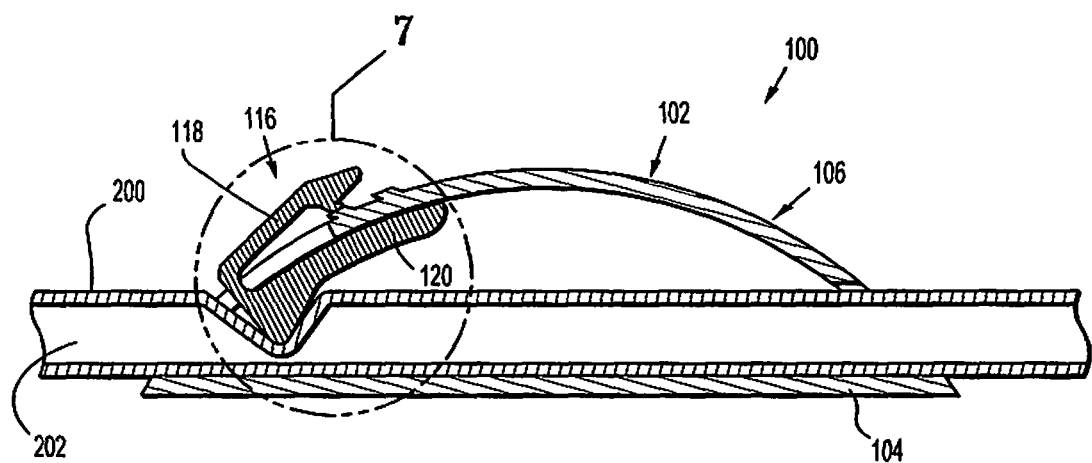
FIG. 6 is a side cross-sectional view of the clamping assembly shown in FIG. 1 with the slide member moving towards the closed position.
Figure 7:
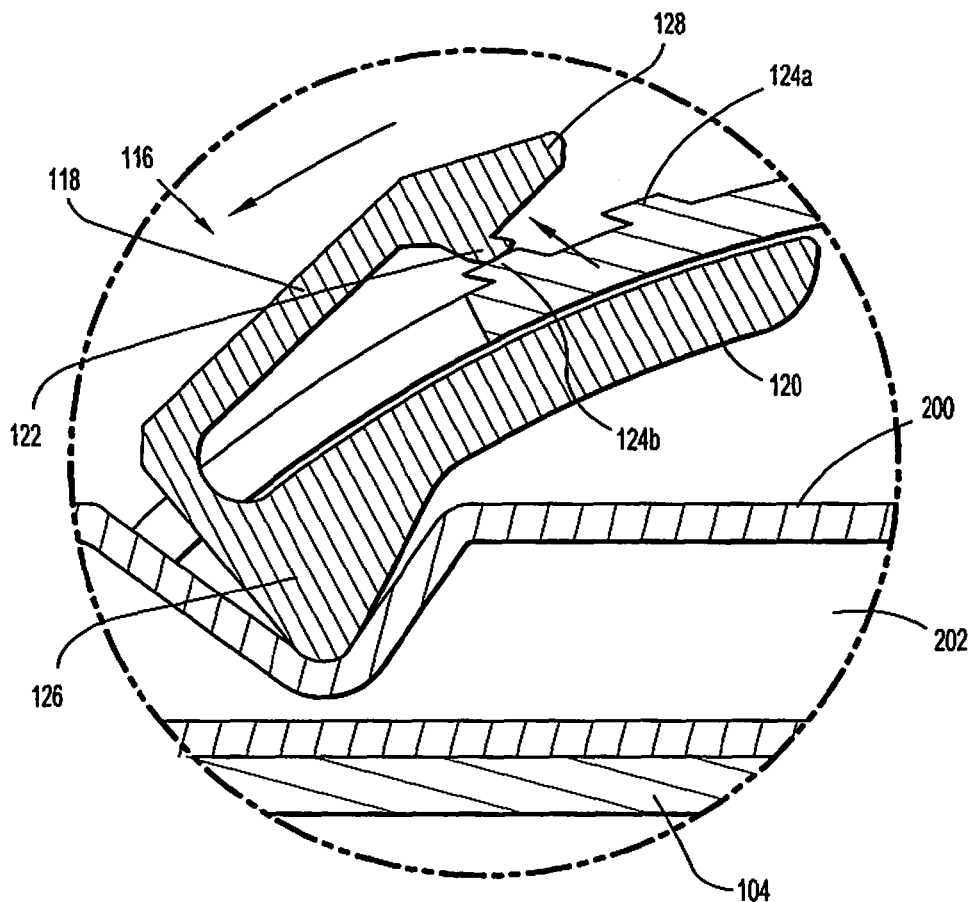
FIG. 7 is an enlarged side cross-sectional view showing the indicated area of detail shown in FIG. 6.

Referring to FIGS. 6 and 7, a clinician can move slide member 116 distally along arcuate portion 106 from the intermediate position to the closed position. During this motion, engagement protrusion 122 slides over detent 124b. While engagement protrusion 122 moves over detent 124b, first portion 118 deflects outwardly from second portion 120 of slide member 116 as shown in FIG. 7. The resilience of slide member 116 allows first and second portions 118, 120 to deflect outwardly from each other and return to their original position after slide member 116 has passed over detent 124b.

Figure 9:
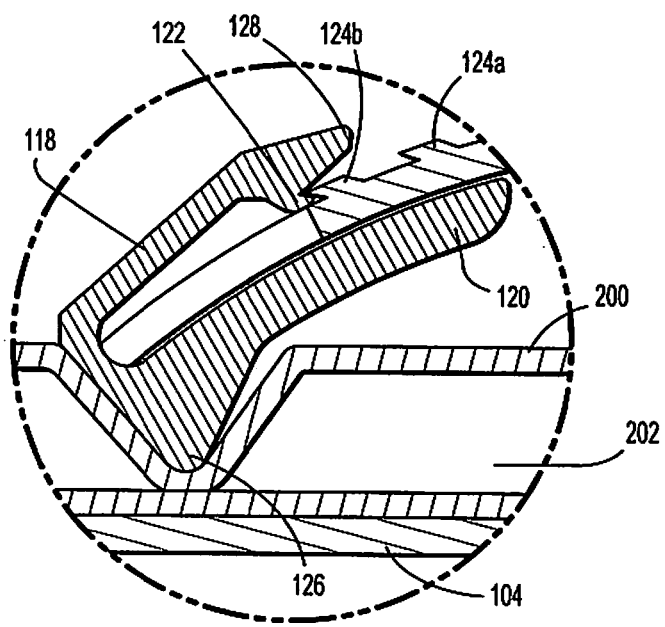
FIG. 9 is an enlarged side cross-sectional view showing the indicated area of detail shown in FIG. 8.

With reference to FIGS. 8 and 9, after engagement protrusion 122 passes over detent 124b, engagement protrusion 122 securely engages detent 124b to lock slide member 116 in the closed position. When slide member 116 is located in the closed position, blunt protuberance 126 presses tubular member 200 against flat base 104 to prevent flow through bore 202 of tubular member 200. As seen in FIG. 9, the pressure exerted by slide member 116 on tubular member 200 collapses a portion of tubular member 200 and completely obstructs flow through bore 202. To release slide member 116 from the intermediate or closed positions, the clinician can deflect engagement member 128 upwardly to separate the first portion 118 of slide member 116 from the second portion 120. Once the first and second portions 118, 120 of slide member 116 have been separated from each other, the clinician can displace slide member 116 along arcuate body portion 106 to the open position or any other desired position.

It will be understood that various modifications may be made to the embodiments of the presently disclosed clamping assemblies. For instance, the presently disclosed clamping assemblies may clamp any conduit capable of transferring fluid from one point to another. Therefore, the above description should not be construed as limiting, but merely as exemplifications of embodiments. Those skilled in the art will envision other modifications within the scope and spirit of the present disclosure.

What is claimed is:

1. A clamping assembly, comprising:
    a body having a base including first and second end portions and an arcuate body portion secured to the base, the arcuate body portion defining at least one opening dimensioned to receive a tubular member having a lumen; and
    a slide member adapted to move within the at least one opening along the arcuate portion between an open position and a closed position, wherein the slide member is movable along the arcuate body portion to compress the tubular member received within the at least one opening against the base to obstruct the lumen of the tubular member when the slide member is in the closed position,
    wherein the arcuate body portion includes a plurality of detents and, each detent being adapted to secure the slide member at a predetermined secured position along the arcuate body portion,
    wherein the slide member includes an engagement member configured to releasably engage a detent of the plurality of detents to retain the slide member in relation to the arcuate body portion, and
    wherein the slide member includes a first portion facing away from the base and a second portion facing toward the base, and the first and second portions of the slide member are configured to spread apart when the slide member moves between predetermined secured positions on the arcuate body portion.

2. The clamping assembly of claim 1, wherein the base is flat and adapted to support the tubular member.

3. The clamping assembly of claim 2, wherein the arcuate body portion is secured to the ends of the base.

4. The clamping assembly of claim 2, wherein a lateral open space is defined between the flat base and the arcuate body portion.

5. The clamping assembly of claim 1, wherein the at least one opening includes a first opening dimensioned to receive the tubular member, the first opening being located in a first section of the arcuate body portion.

6. The clamping assembly of claim 5, further including a second opening located in a proximal section of the arcuate body portion.

7. The clamping assembly of claim 1, wherein the arcuate body portion includes at least one feature which is releasably engagable with a corresponding feature on the slide member to releasably secure the slide member in the closed position.

8. The clamping assembly of claim 1, wherein the second portion of the slide member includes a blunt protuberance configured to compress the tubular member.

9. The clamping assembly of claim 1, further comprising a track positioned along the arcuate body portion, wherein the track is configured to slidably receive the second portion of the slide member to facilitate movement of the slide member along the arcuate body portion.

10. The clamping assembly of claim 1, wherein the slide member is made of a resilient material.

11. The clamping assembly of claim 1, wherein the slide member has a substantially C-shape.

12. The clamping assembly of claim 1, wherein the plurality of detents includes a detent positioned to retain the slide member at an intermediate position between the open and closed positions.

* * * * *